United States Patent [19]

Wilson

[11] Patent Number: 4,537,351
[45] Date of Patent: Aug. 27, 1985

[54] LIQUID AIR FRESHENER DISPENSER
[75] Inventor: Daniel C. Wilson, Taylors, S.C.
[73] Assignee: The Dow Chemical Company, Midland, Mich.
[21] Appl. No.: 513,551
[22] Filed: Jul. 14, 1983
[51] Int. Cl.³ .............................................. A61L 9/04
[52] U.S. Cl. .................................... 239/43; 239/51.5; 239/59
[58] Field of Search ....................... 239/34, 37, 39–44, 239/49, 51.5, 57–59; 222/548, 553

[56] References Cited

U.S. PATENT DOCUMENTS

| | | | |
|---|---|---|---|
| 436,130 | 9/1980 | Gubelman | 239/42 |
| 1,099,720 | 6/1914 | Peck | 239/40 |
| 1,755,901 | 4/1930 | Searle | 239/39 |
| 1,816,442 | 7/1931 | Reefer | 239/42 |
| 1,818,684 | 8/1931 | Blechman | 239/42 |
| 1,974,414 | 9/1934 | Dupuy | 239/42 |
| 2,166,969 | 7/1939 | Rooch | 239/42 |
| 2,481,296 | 9/1949 | Dupuy | 239/42 |
| 2,586,179 | 2/1952 | Rooch | 239/42 |
| 2,966,286 | 12/1960 | Moran | 222/553 |
| 4,323,193 | 4/1982 | Compton | 239/44 |

Primary Examiner—Andres Kashnikow
Assistant Examiner—James R. Moon, Jr.
Attorney, Agent, or Firm—Trexler, Bushnell & Wolters, Ltd.

[57] ABSTRACT

A simplified vaporizing dispenser features snap attachment of a base cap to an inverted container, positive "ON" and "OFF" adjustments for the respective activation and deactivation of the dispenser, the use of an absorbent sheet shaped in the form of the frustum of a cone with the narrow end inserted in an annular well for isolating the wetting area of the absorbent material from the vaporizing area and thereby enabling waving of the dispenser about in the air without spilling liquid, and an outer decorative sleeve that enables adjustment in the emitted vapor level.

14 Claims, 7 Drawing Figures

LIQUID AIR FRESHENER DISPENSER

BACKGROUND OF THE INVENTION

1. Field of the Invention

The present invention relates to air fresheners, and more particularly, to an inverted liquid system for providing a controlled release of fragrance to the environment.

2. Description of the Prior Art

Inverted liquid systems for diffusing to the air in a room the vapor of a volatile liquid have long been known to the art. Such dispensers have been employed for deodorizing and purifying the air, for the suppression or extermination of moths or the prevention of their destructive action upon furs and fabrics, and for other purposes including disinfection.

Typically, the prior art inverted liquid systems have comprised an inverted bottle supported within a perforated sleeve with the mouth of the bottle positioned a short distance above the bottom of a cup or pan and with absorbent material within the sleeve extending into the cup. Volatile liquid from the bottle flows into the cup until the level reaches the mouth of the bottle where the flow is stopped by atmospheric pressure. As soon as the liquid level falls below the mouth of the bottle due to evaporation, flow from the bottle starts again and, as a result, the liquid level is maintained at the level of the mouth of the bottle. Liquid picked up by the absorbent material vaporizes and diffuses to the atmosphere through the perforated sleeve. The U.S. patents identified in the following list disclose a representative sample of such prior art inverted liquid systems:

| | | | |
|---|---|---|---|
| Gubelman | 436,130 | Dupuy | 1,974,414 |
| Peck | 1,099,720 | Rooch | 2,166,969 |
| Searle | 1,755,901 | Dupuy | 2,481,296 |
| Blechman | 1,818,684 | Rooch | 2,586,179 |

Various provisions have been made in the prior art inverted liquid system dispensers for preventing the evaporation of the liquid until it is desired to actuate the dispenser. These provisions have included using a screw threaded neck for the bottle and a removable cap or closure having screw threads as in U.S. Pat. Nos. 1,755,901, 1,818,648, 1,974,414, 2,166,969 and 2,586,179.

The use in the prior art inverted liquid system dispensers of screw threaded bottle necks and closures has added undesirably to the complexity and manufacturing cost thereof and also has limited their usefulness. A problem in this connection is that once the dispenser has been activated, the vaporization process cannot be stopped and continues until all of the liquid has been evaporated. Another problem, one which limits the usefulness of the dispenser, is a tendency for liquid to spill therefrom if the dispenser is waved in the air to provide a burst release of fragrance.

Thus, there remains a need and a demand in the art for further improvements in inverted liquid system air freshener dispensers.

SUMMARY OF THE INVENTION

An object of the invention is to provide an improved and simplified inverted liquid system dispenser which is not subject to the aforementioned drawbacks of the prior art dispensers.

Another object of the invention is to provide such an improved dispenser that enables fragrance to be released at a uniform rate over the life of the product and the activity of which can be discontinued when not needed, nor desired, and reactivated at a later date.

A further object of the invention is to provide such an improved dispenser that may be waved around without spilling liquid, to increase the contact between the vaporized liquid and the air to provide a burst release of fragrance when such is needed to deal with the sudden generation of a greater than normal amount of unpleasant odor.

Still another object of the invention is to provide such an improved dispenser in which the emitted fragrance level is adjustable.

In accomplishing these and other objectives of the invention, there is provided an inverted liquid system dispenser that includes an inverted container or bottle having a neck forming a mouth therefor and which is supported by a plastic base by snap attachment means, all screw threads having been eliminated. The dispenser is characterized in having positive "ON" and "OFF" positions, as described hereinafter. Two transverse diametrically opposed holes are provided in the neck of the container for the flow of liquid therefrom. The base has an annular well in the center of which is a reentrant portion or plug that extends into the mouth and neck of the container. Transverse diametrically opposed slots on the plug cooperate with the transverse holes on the neck to allow the flow of liquid from the container or to turn it off, a quarter turn only of the container with respect to the base being required to effect an adjustment from the fully opened position wherein the transverse openings of the plug and the neck are in register or alignment to the fully closed position wherein the transverse openings of the plug and the neck are out of register or alignment. An undulating ring seal provided interiorly of the neck of the container enables a positive closure or turn off of the liquid from the container.

A sleeve of absorbent material such as blotting paper in the form of a frustum of a cone and provided with the narrow end extending into the annular well of the base, is squeezed against the outer wall of the annular well by a peripheral ring or lip on the neck of the container. As a result, liquid flowing from the mouth of the container through the opposed sets of holes in the neck and slots on the plug is retained in the well except for the liquid absorbing action of the blotting paper due to capillary attraction. Thus, when the dispenser is in its activated or "ON" state, the liquid within the annular well is somewhat isolated from the ambient atmosphere. With this arrangement liquid is prevented from being spilled from the dispenser when the latter is waved to provide a burst of fragrance.

Further, in accordance with the invention, an inner upstanding sleeve or base cap is molded as part of the base and is provided at its upper end with two diametrically opposed elongated slots. Diametrically opposed lugs on the container fit within the slots on the inner sleeve and provide and cooperate therewith upon relative angular rotation of the container and base to provide positive "ON" and "OFF" positions for the dispenser. A single internal bead at the top of the inner sleeve cooperates with external beads on the container for snap attachment of the container to the base, locking of the container to the base, however, being effected by the lugs and not the beads.

The inner sleeve is provided with three circumferential rows of elongated slots for allowing the vaporizing fragrance of the liquid absorbed by the conical sleeve to escape. A perforated outer sleeve is provided over the inner sleeve for decorative purposes and also for enabling the emitted fragrance level to be adjusted.

In the operation of the dispenser, liquid passing through the holes in the container neck and slots in the plug flows into the annular well and wets the portion of the conical absorption material extending therein. Liquid flows as long as there is access of air through the holes in the container neck and slots in the plug to relieve the partial vacuum that is created in the container by the flow of liquid therefrom. Thus, when the level of liquid in the annular well covers the holes in container neck, the flow is stopped. Capillary attraction causes the liquid in the annular well to be drawn up into the absorption material above the ring or lip on the container neck. Vaporization of the absorbed liquid in the absorption material releases the fragrance. As the level of liquid in the annular well drops, the holes in the container neck and slots in the plug are uncovered. This allows a further flow of liquid into the annular well from the container.

BRIEF DESCRIPTION OF THE DRAWINGS

Having summarized the invention, a detailed description follows with reference being made to the accompanying drawings which form part of the specificiation, of which.

DESCRIPTION OF THE PREFERRED EMBODIMENT

Figure 1:
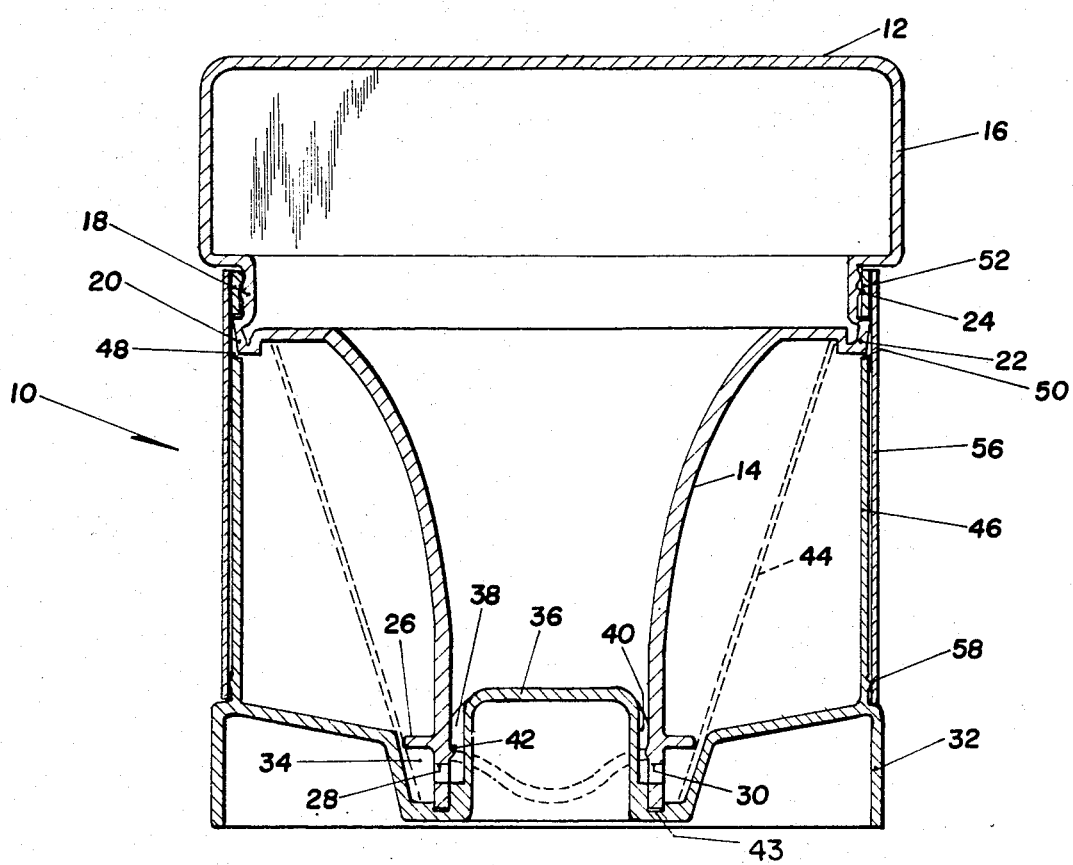
FIG. 1 is a sectioned elevational view of a liquid air dispenser according to the invention.

The dispenser indicated at 10 in FIG. 1 includes a container 12 in the form of a bottle desirably molded as a unitary member of high density polyethylene. Container 12 includes an elongated tapering neck portion 14, a cylindrical base portion 16, and a short cylindrical portion 18 of reduced diameter between the neck portion 14 and the base portion 16. A lug 20 is provided on one side of cylindrical portion 18 and a lug 22 is provided on the diametrically opposite side thereof. Between lugs 20 and 22 and cylindrical base 16 a plurality of beads 24 are provided on cylindrical portion 18.

A projecting container lip or ring 26 is provided on neck portion 14 of container 12 spaced somewhat from the end thereof. At the end of neck portion 14 there are also provided diametrically opposed holes or orifices 28 and 30.

Figure 3:
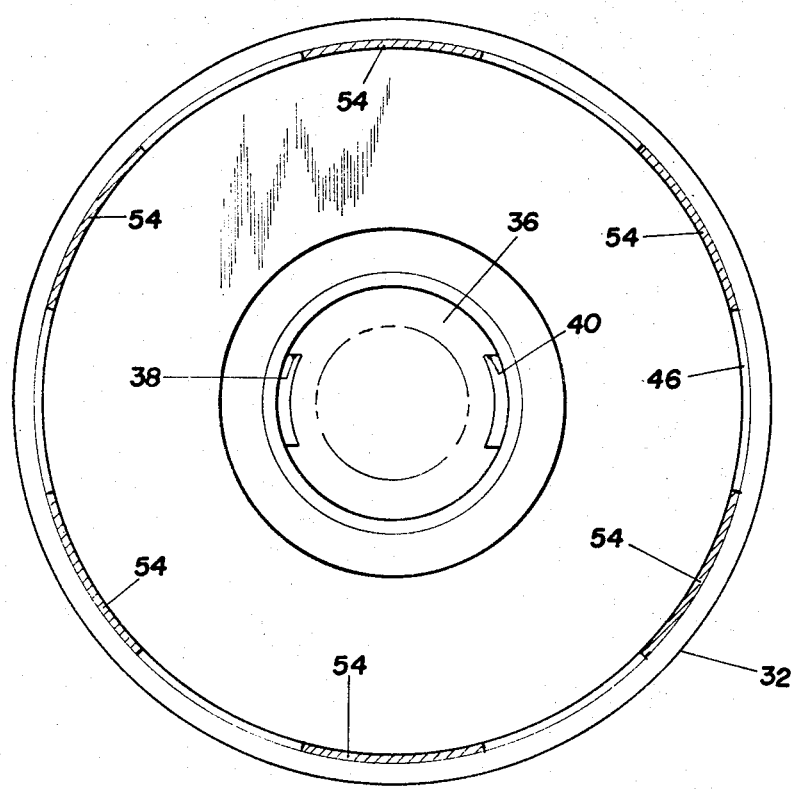
FIG. 3 is a top view of the base of the dispenser with the container removed.
Figure 4:
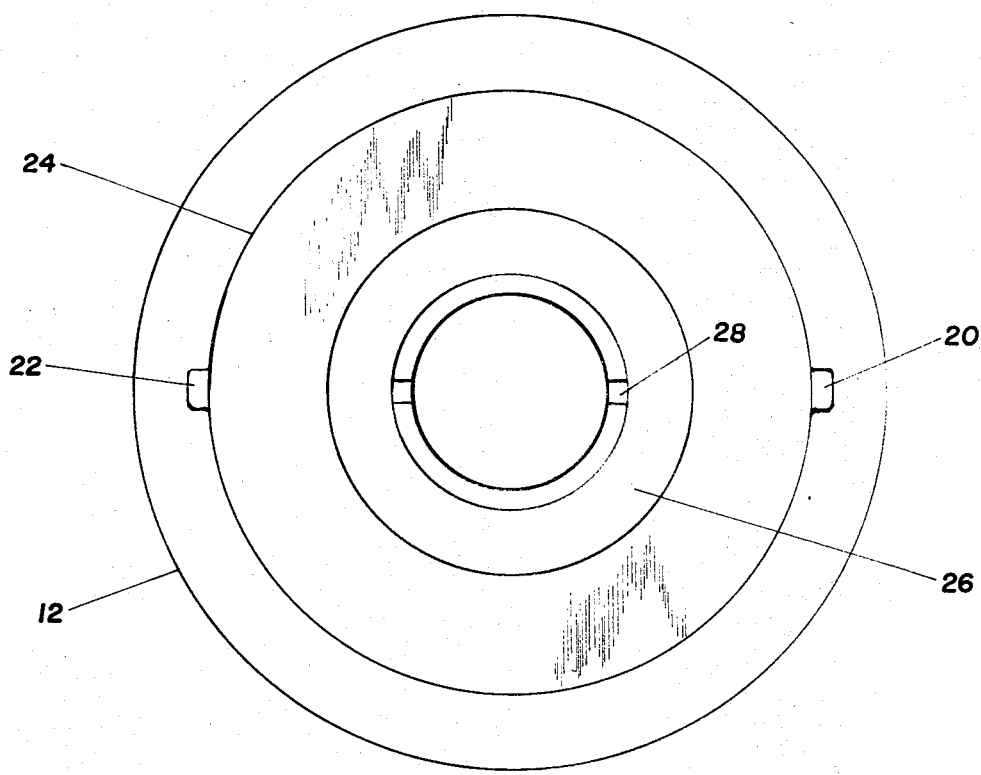
FIG. 4 is a bottom view of the container.
Figure 5:
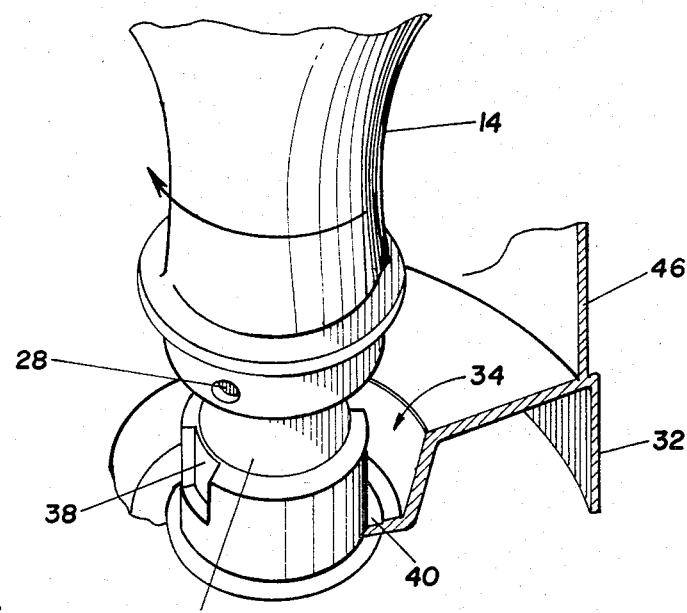
FIG. 5 is a perspective view of a portion of the dispenser with the reentrant portion or plug of the base cap removed from the neck of the container.

The container 12 is adapted to contain any desired liquid to be vaporized and in use rests in an inverted position on a plastic closure or base cap 32 that desirably is molded as a single unitary member of polypropylene. The base cap 32 includes an annular well 34 in the center of which is located a cylindrical reentrant portion or plug 36. Plug 36, as shown in FIG. 1, is inserted in the end of neck 14 of container 12, forming a liquid tight fit therewith. Diametrically opposed slots or grooves 38 and 40 on plug 36, as shown in FIGS. 1, 3 and 5, extend part way only into annular well 34. Slots 38 and 40 cooperate, respectively, with holes 28 and 30 to allow liquid to flow from container 12 into the annular well 34 or to stop such flow of liquid depending upon the relative angular position of base cap 32 with respect to container 12. Thus, a quarter turn of base cap 32 relatively to container 12 is sufficient to adjust the openings 28, 38 and 30, 40 from a position of registration or alignment allowing a flow of liquid from container 12 to annular well 34 to a position of non-alignment wherein such flow of liquid is precluded or shut off.

Figure 2:
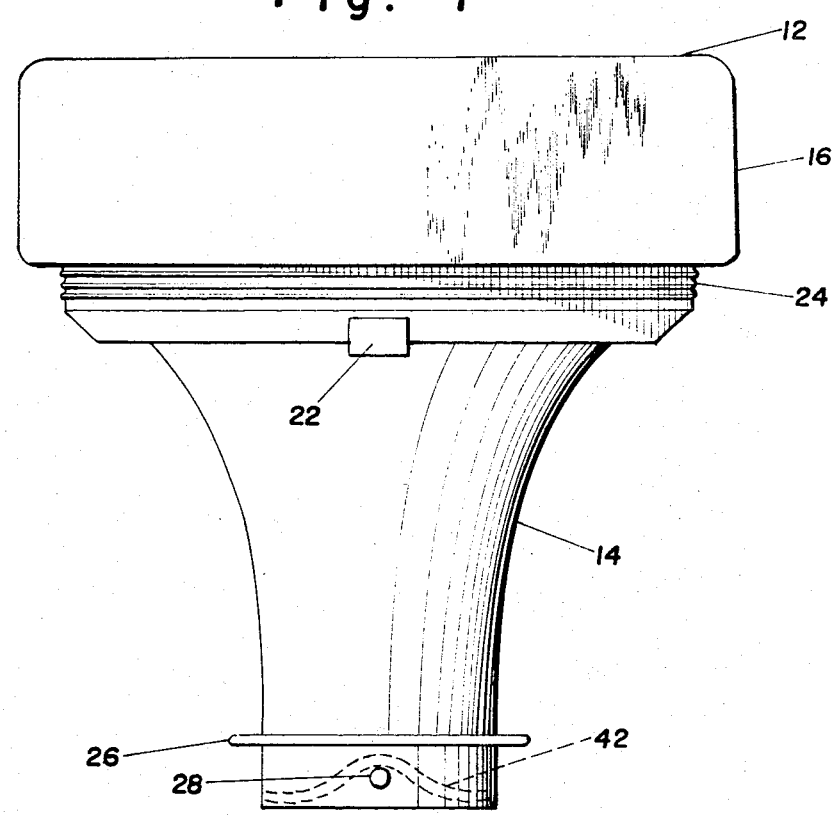
FIG. 2 is a side elevational view of the inverted container of FIG. 1.

For ensuring a positive shutoff of liquid flow in the non-aligned position of the openings 28, 38 and 30, 40, a ring seal 42 having a wave or undulation therein is provided on the interior wall of the neck 14 of container 12, as shown in FIGS. 1 and 2. The undulation of ring seal 42 is so positioned as to provide an effective seal for holes 28 and 30 in the non-aligned position thereof.

Thus, with the slots 38 and 40 out of alignment with the respectively associated holes 28 and 30, it will be evident that a seal in the region of each of the holes 28 and 30 will be effected between the plug 36 and the interior surface of neck 14 at a position with respect to the neck 14 that is inward of the holes 28 and 30. At the same time, a seal will be effected between the plug 36 and the interior surface of the neck 14 in the region of each of the slots 38 and 40 at a position with respect to the neck 14 that is outward of the holes 28 and 30. In the latter regions, the seal is effected at the side wall of the plug 36 between the bottom of the annular well 34 and the slots 38 and 40.

A ring seal 43 may also be provided on the bottom of annular well 34, as seen in FIG. 1. The end of neck 14 engages seal ring 43 in a sealing manner.

Absorption material 44, which may comprise blotting paper formed in the shape of the frustum of a cone, has the smaller end inserted in the annular well 34 squeezed between the container lip or ring 26 and the outer wall of annular well 34. Thus the area of the absorption material 44 that is adapted to be wet by the liquid, specifically that area below the lip 26 on neck 14 of container 12, is effectively isolated from the area of the material 44 above the lip 26 from which vaporization takes place. Being conical in form, the absorption material 44 is characterized in providing a larger absorbing and vaporizing area for the same vertical height thereof.

The base cap 32 further includes an upstanding sleeve 46 which for convenience hereinafter is termed an inner sleeve. Inner sleeve 46 is integrally molded with base cap 32 and is provided at the upper end thereof with two diametrically opposed elongated slots 48 and 50 with which the lugs 20 and 22 on the container portion 18 cooperate to provide positive activated and deactivated, that is, "ON" and "OFF", positions, respectively, for the dispenser 10. A single bead 52 on the upper peripheral inner edge of sleeve 46 cooperates with one of the beads 24 on the container portion 18 for snap attachment and firm retention of the container 12 to the base cap 32 with desired squeezing of the absorbent material 44 by the bottle lip or ring 26, locking of the container 12 to the base cap 32, however, being effected by lugs 20 and 22 and slots 48 and 50 respectively associated therewith.

Figure 6:
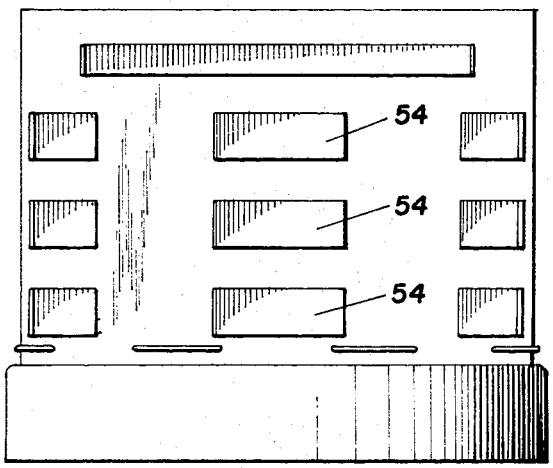
FIG. 6 is a side view of the base cap of the dispenser.

The inner sleeve, as best seen in FIGS. 3 and 6, is provided with three circumferential rows of elongated slots 54 for allowing the vaporizing fragrance to escape.

Figure 7:
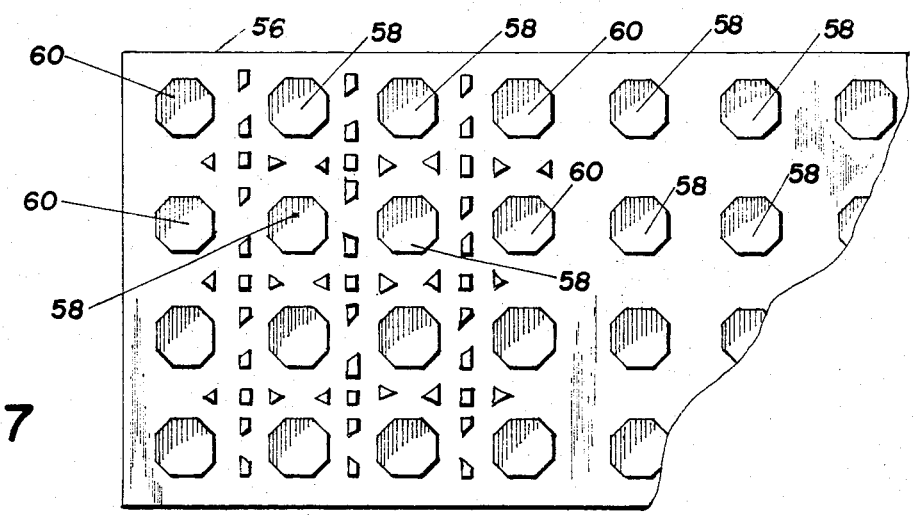
FIG. 7 is a fragmented view illustrating a development of the outer sleeve according to the invention.

In accordance with the invention, a perforated outer sleeve 56 is provided in association with the inner sleeve 46 for providing adjustability in the emitted fragrance level and also for decorative purposes. A detail of the outer sleeve 56, which may be made of printed and die cut paperboard, is shown in FIG. 7. Four circumferential rows of spaces may be provided with each row having eighteen spaces. Adjacent pairs of spaces indicated at 58 may be punched out in each row with a solid space 60 retained between each punched out pair of spaces, thus providing twelve holes in each row and a total of forty-eight holes in the outer sleeve 56. A plurality of circumferentially spaced interference bumps 58 are provided adjacent the lower end of inner sleeve 46 to hold the outer sleeve 56 on during assembly of the dispenser 10.

By relative rotation of outer sleeve 56 with respect to the inner sleeve 46, the total or effective size of the perforations through the sleeves 46 and 56 may be adjusted to vary the rate of vaporization, and hence, the level of fragrance emitted by the dispenser 10.

In the activated condition of the dispenser 10, effected by relative rotation of the container 12 and base cap 32 to a first extreme position to bring transverse container slots 28 and 30 into alignment with the respectively associated transverse slots 38 and 40 of plug 36 of base cap 32, liquid is allowed to flow from container 12 into the annular well 34, as seen in FIG. 1, to wet the lower end of the absorption material 44. Such flow continues as long as there is access of air through the aligned hole 28, 38 and slots 30, 40 to relieve the partial vacuum created in the container 12 by the flow of liquid therefrom, that is, until the level of liquid in the annular well 34 covers the aligned pairs of slots. The absorbent material 44 becomes saturated with the liquid and the liquid evaporates therefrom and comingles with the ambient air in the room. That is to say, vaporization of the absorbed liquid from the absorbent material 44 releases the fragrance which is diffused to the environment through the perforations in the inner sleeve 46 and the outer sleeve 56. Absorption of the liquid in the annular well 34 by the absorbent material 44 and subsequent drying of the latter due to vaporization cause the level of liquid in the annular well 34 to drop to uncover the transverse aligned holes 28, 38 and slots 40, 40, and hence, to allow a further flow of liquid from the container 12. By this means there is maintained a uniform release of fragrance to the environment by the dispenser 10 as long as there is liquid in the container 12 and the dispenser is maintained in its activated state.

While in the activated state thereof, the level of fragrance emitted by the dispenser may be adjusted by relative rotation of the outer sleeve 56 and the inner sleeve 46 to increase or decrease the registration of the holes 58 in the outer sleeve 56 with the slots 54 in the inner sleeve 46.

Since the liquid within the annular well 34 is contained therein by the container lip or ring 26 squeezing against the absorption material 44, liquid is prevented from spilling from the dispenser 10 if the dispenser is inverted or waved about to provide a burst of freshening air. This feature of largely isolating the liquid within the annular well 34 from the surrounding air also contributes to uniformity of vaporization and controlled adjustability in the level of fragrance emitted by the dispenser 10.

In the inactivated condition of the dispenser 10, effected by relative rotation of container 12 and base cap 32 to a second extreme position, the transverse pairs of holes 28, 30 and slots 38, 40 of the container 12 and plug 36 of base cap 32 are non aligned and the plug 36 is in liquid tight engagement with the end of the neck 14 of the container 12. As a result, liquid in the annular well 34 is not replenished as it is absorbed by the absorbent material 44 and vaporized therefrom. Consequently, the vaporizing action of the dispenser 10 stops. The arrangement is such that the vaporizing action of the dispenser 10 may be discontinued at any time when not needed, nor desired, and reactivated at a later date.

Thus, there is provided according to the invention, an improved inverted liquid system dispenser which provides uniform release of fragrance, which provides adjustability in the fragrance level emitted, which may be waved about to provide a burst of fragrance, and in which the release of fragrance can be discontinued when not needed, nor desired, and reactivated at a later date. The dispenser of the invention further is characterized by the simplicity of the structure thereof, the screw threaded members required for assembly of the prior art dispensers having been eliminated, the container snapping to the base and having positive "ON-OFF", and the absorption member being made in the form of a frustum of a cone thereby providing a greater absorption and vaporizing area for the same vertical height of the absorption member.

What is claimed is:

1. A vaporizing device comprising,
   a base, said base including a perforated sleeve, a cylindrical plug and an annular well with said plug being located substantially centrally of said well and having diametrically opposed slots formed therein,
   a container having a neck forming a mouth therefor, said neck having transverse diametrically opposed holes therein,
   said container being mounted in inverted position on said base with said plug inserted in said neck thereof and with said sleeve being positioned in surrounding relation to at least a portion of said container, and
   absorbent material positioned between said neck of said container and said sleeve and having a portion thereof extending into said annular well,
   said base being angularly adjustable with respect to said container between two positions in one of which positions said transverse slots of said plug are out of alignment with the transverse holes in said neck and a liquid tight seal is effected between said plug and said neck whereby the flow of liquid out of said container is precluded, and in the other of which positions said transverse slots of said plug are in alignment with said transverse holes in ssid neck whereby liquid is allowed to flow from said container into said annular well to wet said portion of said absorbent material as long as there is access of air through the transverse slots of said plug and the holes of said neck to relieve the partial vacuum created in the container by the flow of liquid therefrom, said annular well having an outer wall and wherein a lip is provided on said neck, said lip being so formed and positioned that with the base in position on said container, said lip squeezes said absorbent material against said outer wall to prevent liquid from spilling from the device if waved about in the air.

2. A vaporizing device as specified in claim 1 wherein said base with said perforated sleeve, said plug and said annular well is formed as a single integrally molded plastic member.

3. A vaporizing device as specified in claim 2 wherein said container includes a base portion and a cylindrical portion adjacent said base portion with said neck tapering from said cylindrical portion to a narrow opening at the mouth of said container, wherein said cylindrical portion of said container includes a plurality of circumferential beads on the external surface thereof, and wherein said sleeve of said base is adapted to fit over said cylindrical portion of said container in snug engagement therewith and is provided with a circumferential bead at the upper inner surface thereof for cooperation with the plurality of beads on the external surface of said cylindrical portion for effecting snap action attachment of said container to said base.

4. A vaporizing device as specified in claim 3 wherein said cylindrical portion of said container includes at least one lug projecting radially therefrom, and wherein said sleeve includes an elongated slot formed near the upper end thereof into which said lug on said cylindrical portion of said container is inserted for limiting the extent to which said base may be angularly adjusted with respect to said container, engagement of said lug with one end of said elongated slot comprising said one position in which flow of liquid from said container into said annular well is precluded, and engagement of said lug with the other end of said elongated slot comprising said other position in which the flow of liquid from said container into said annular well is allowed.

5. A vaporizing device as specified in claim 4 wherein said cylindrical portion of said container includes two diametrically opposing lugs projecting radially therefrom, and wherein said sleeve includes two diametrically opposing elongated slots with one of said lugs on said cylindrical portion being inserted into one of said elongated slots and the other one of said lugs being inserted into the other one of said elongated slots.

6. A vaporizing device as specified in claim 3 wherein said absorbent material has the shape of the frustum of a cone with the narrow end thereof inserted in said annular well.

7. A vaporizing device as specified in claim 5 wherein said absorbent material has the shape of the frustum of a cone with the narrow end thereof inserted in said annular well and with the upper end thereof resting against said lugs.

8. A vaporizing device as specified in claim 3 further including a decorative perforated outer sleeve provided in association with said integrally molded sleeve of said base, relative rotation of said sleeves to bring the perforations thereof into or out of registration permitting adjustment in the effective size of the total perforations, and hence, in the rate of vaporization of absorbed liquid from said absorbent material.

9. A vaporizing device comprising, a base, said base including a perforated sleeve, a cylindrical plug and an annular well with said plug being located substantially centrally of said well and having diametrically opposed slots formed therein, a container having a neck forming a mouth therefor, said neck having transverse diametrically opposed holes therein, said container being mounted in inverted position on said base with said plug inserted in said neck thereof and with said sleeve being positioned in surrounding relation to at least a portion of said container, and absorbent material positioned between said neck of said container and said sleeve and having a portion thereof extending into said annular well, said base being angularly adjustable with respect to said container between two positions in one of which positions said transverse slots of said plug are out of alignment with the transverse holes in said neck and a liquid tight seal is effected between said plug and said neck whereby the flow of liquid out of said container is precluded, and in the other of which positions said transverse slots of said plug are in alignment with said transverse holes in said neck whereby liquid is allowed to flow from said container into said annular well to wet said portion of said absorbent material as long as there is access of air through the transverse slots of said plug and the holes of said neck to relieve the partial vacuum created in the container by the flow of liquid therefrom, said device further including a ring seal between the cylindrical plug of said base and the interior wall of the neck of said container to provide a positive shut off of liquid from said container with the slots in said plug out of alignment with the holes in said neck, and wherein the opposed slots in said plug extend part way only into said annular well, and wherein said ring seal has an undulation therein such that, with the slots in said plug out of alignment with the holes in said neck, a seal in the region of each of the holes is effected between said plug and said neck at a position with respect to said neck that is inward of said holes, and a seal in the region of each of the slots is effected between said plug and said neck at a position with respect to said neck that is outward of said holes.

10. A vaporizing device as specified in claim 9 wherein said base with said perforated sleeve, said plug and said annular well is formed as a single integrally molded plastic member, and wherein said container includes a base portion and a cylindrical portion adjacent said base portion with said neck tapering from said cylindrical portion to a narrow opening at the mouth of said container, wherein said cylindrical portion of said container includes a plurality of circumferential beads on the external surface thereof, and wherein said sleeve of said base is adapted to fit over said cylindrical portion of said container in snug engagement therewith and is provided with a circumferential bead at the upper inner surface thereof for cooperation with the plurality of beads on the external surface of said cylindrical portion for effecting snap action attachment of said container to said base.

11. A vaporizing device as specified in claim 10 wherein said cylindrical portion of said container includes two diametrically opposing lugs projecting radially therefrom, and wherein said sleeve includes two diametrically opposing elongated slots formed near the upper end thereof with one of said lugs on said cylindrical portion of said container being inserted into one of said elongated slots and the other one of said lugs being inserted in the other one of said elongated slots, for limiting the extent to which said base may be angularly adjusted with respect to said container, engagement of each of said lugs with one end of the elongated slot associated therewith comprising said one position in which flow of liquid from said container into said annular well is precluded, and engagement of each of said lugs with the other end of the elongated slot associated therewith comprising said other position in which the flow of liquid from said container into said annular well is allowed.

12. A vaporizing device as specified in claim 11 wherein said absorbent material has the shape of the frustum of a cone with the narow end thereof inserted in said annular well, wherein said annular well has an outer wall and wherein a lip is provided on said neck of said container, said lip being so formed and positioned that with said base snapped in position to said container said lip squeezes said absorbent material against said outer wall of said annular well to prevent liquid from spilling from said device if waved about in the air.

13. A vaporizing device as specified in claim 11 wherein said lugs on said cylindrical portion of said container include a portion projecting in the direction of said neck of said container, wherein said absorbent material has the shape of the frustum of a cone with the narrow end thereof inserted in said annular well and with the upper end thereof resting against said lugs, wherein said annular well has an outer wall, and wherein a lip is provided on said neck of said container, said lip being so formed and positioned that with said base snapped in position to said container said lip squeezes said absorbent material against said outer wall of said annular well to prevent liquid from spilling from said device if waved about in the air.

14. A vaporizing device comprising, a base, said base including a perforated sleeve, a cylindrical plug and an annular well with said plug being located substantially centrally of said well and having diametrically opposed slots formed therein, a container having a neck forming a mouth therefor, said neck having transverse diametrically opposed holes therein, said container being mounted in inverted position on said base with said plug inserted in said neck thereof and with said sleeve being positioned in surrounding relation to at least a portion of said container, and absorbent material positioned between said neck of said container and said sleeve and having a portion thereof extending into said annular well, said base being angularly adjustable with respect to said container between two positions in one of which positions said transverse slots of said plug are out of alignment with the transverse holes in said neck and a liquid tight seal is effected between said plug and said neck whereby the flow of liquid out of said container is precluded, and in the other of which positions said transverse slots of said plug are in alignment with said transverse holes in said neck whereby liquid is allowed to flow from said container into said annular well to wet said portion of said absorbent material as long as there is access of air through the transverse slots of said plug and the holes of said neck to relieve the partial vacuum created in the container by the flow of liquid therefrom, and means for preventing liquid from spilling from said well if the device is inverted to provide a burst of freshening air.

* * * * *